United States Patent [19]

Stark

[11] 4,135,528

[45] Jan. 23, 1979

[54] INTERDENTAL STIMULATOR

[75] Inventor: Marvin M. Stark, Los Altos Hills, Calif.

[73] Assignee: Marvin M. Stark Research Foundation, Santa Clara, Calif.

[21] Appl. No.: 783,184

[22] Filed: Mar. 31, 1977

[51] Int. Cl.² ............................................. A61C 15/00
[52] U.S. Cl. ...................................................... 132/89
[58] Field of Search .................................... 132/89–93

[56] References Cited

U.S. PATENT DOCUMENTS

| | | | |
|---|---|---|---|
| 3,563,253 | 2/1971 | Barman | 132/89 |
| 3,910,293 | 10/1975 | Lemelson | 132/89 |
| 3,978,872 | 9/1976 | Bond | 132/89 |

Primary Examiner—G.E. McNeill
Attorney, Agent, or Firm—Lothrop & West

[57] ABSTRACT

An interdental stimulator for use with human teeth in situ is formed of a stick of clear wood, preferably European sycamore, elongated in the direction of the wood grain and for the most part being substantially rectangular in transverse cross-section. One end portion of the stick is conformed to define two mutually inclined, longitudinally extending, approximately planar side surfaces. This end portion is substantially triangular in transverse cross-section and is truncated to form an inclined planar surface opposite the apex or ridge of the triangular portion. The end portion in transverse cross-section is of a size to be at least partly received in the normal interproximal spaces between human teeth.

3 Claims, 5 Drawing Figures

INTERDENTAL STIMULATOR

BRIEF SUMMARY OF THE INVENTION

Various forms of toothpicks and the like have for years been utilized in connection with the cleaning of the interproximal spaces of human teeth. In more recent years it has been determined that there is considerable value not only in keeping the interproximal spaces clean but also in massaging the gums or gingival surfaces from time to time. While the benefit of massaging action is by no means limited thereto, it is of special use in connection with the care of the teeth and mouth in younger people. There is often a need for a similar treating device in connection with the teeth of those who have undergone substantial periodontal surgery. Many known toothpicks are of metal or like rigid material which sometimes may be injurious and many are of woods that tend to fracture or splinter when utilized, sometimes doing more harm than good. In the present instance there is provided a massaging or stimulating device which can be utilized also as a cleaning structure for the interproximal spaces and for the adjacent tissues, the device being formed of a specially chosen wood not subject to fraying or splintering and having other beneficial attributes. The wood is shaped so that it can be introduced well into the normal or even abnormal interproximal spaces in human dentition and has appropriate surfaces for the stimulating and massaging action desired.

DETAILED DESCRIPTION

Figure 1:
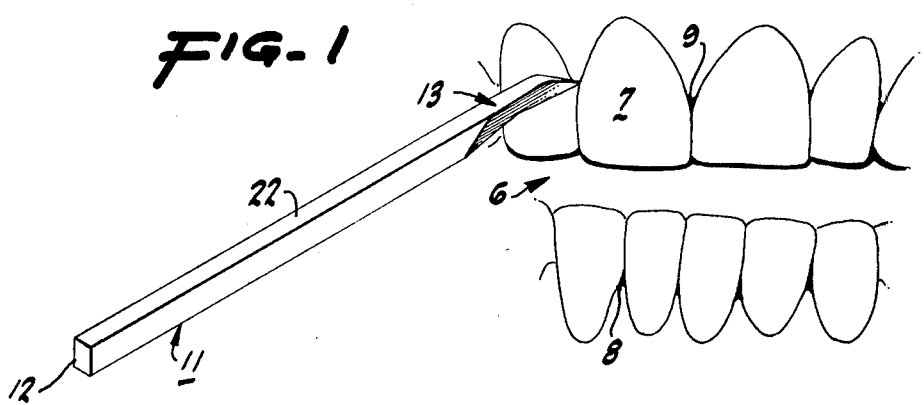
FIG. 1 is an elevation, portions being broken away, of a portion of the human mouth, the interdental stimulator of the invention being shown in isometric perspective.
Figure 2:
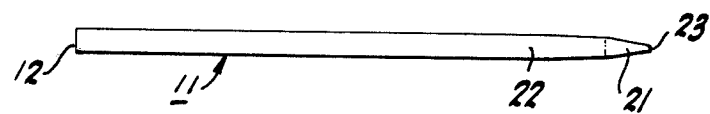
FIG. 2 is a plan, from the top, of the interdental stimulator.

While the interdental stimulator of the invention can be embodied in widely variant ways, it has with considerable success been embodied substantially as shown herein. The general utility is in connection with the human mouth 6 containing normal human teeth 7 having the customary interproximal spaces 8 therebetween, although in the case of extensive periodontal surgery the spaces 8 may vary substantially from those illustrated. The spaces are bounded by the teeth 7 and also by the surfaces 9 of the gingiva or gums.

For use as an interdental stimulator, there is provided a relatively straight stick 11 of wood. There are only a few woods that are particularly useful in this connection, and the one preferred herein is a sycamore which is obtained from trees in the Black Forest in Germany and some adjacent areas of Switzerland. This wood is referred to herein as European sycamore. It is not to be confused with other so-called sycamores from Asia or from the United States.

The straight stick 11 is of the clear European sycamore wood and is elongated in the general direction of the natural wood grain. For the most part of its length the stick in transverse cross-section is rectangular or square, as shown by the configuration of one end 12 thereof.

Figure 4:
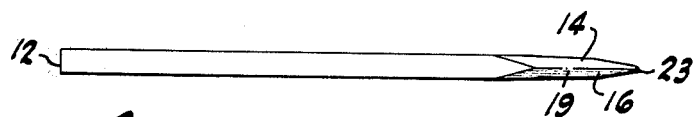
FIG. 4 is a bottom plan view of the interdental stimulator.
Figure 5:
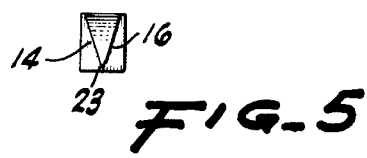
FIG. 5 is front end elevation of the interdental stimulator.

The other end portion 13 of the stick is especially configured. The precise shape does not conform to usual geometrical terms, but is approximated by a geometrical description thereof. The end portion 13 is reduced to a triangular cross-section, two sides of which are formed by a pair of mutually inclined, longitudinally extending, approximately planar side surfaces 14 and 16 (FIG. 4). These surfaces 14 and 16 are not exactly planar since they are in part concave or slightly conical, but result in a shape in transverse cross-section that is triangular with the apex 17 of the triangle defining a longitudinally extending ridge.

Figure 3:
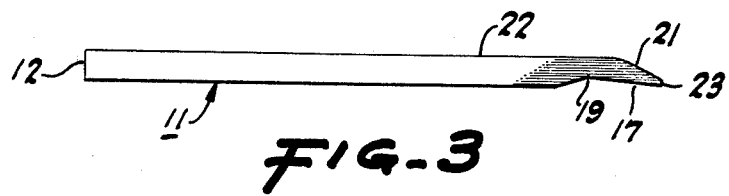
FIG. 3 is a side elevation showing one side of the stimulator, the other side being reversely symmetrical with respect thereto.

The transverse cross-section of the triangular portion varies in dimension along the length of the stick to leave the apex or ridge 17 inclined with respect to the otherwise straight portion of the stick. In effect, this leaves a reentrant, approximately dihedral portion 19, as especially shown in the side elevation of FIG. 3. Finally, the tip of the stick is truncated to provide a generally planar, triangular surface 21 extending from the otherwise uninterrupted top surface 22 of the stick to a slightly rounded point 23 at the apex of the stick and particularly as a terminus of the end portion 13.

The actual dimensions of the configured end portion 13 are such that the apex 17 is readily received in relatively small interproximal spaces, whereas the larger portions of the triangular terminus 13 are effective in connection with larger interproximal spaces, especially those which may have resulted from periodontal surgery.

In use, the interdental stimulator is positioned substantially as shown in FIG. 1 and is worked into and through each of the interproximal spaces and particularly is rubbed against the adjacent gingival surfaces. Although there is substantial force and friction involved, it is a property of the European sycamore that the wood does not shatter or splinter or fray to the detriment of the user. Furthermore, the wood, although originally hard, tough and elastic, does absorb some oral moisture and becomes softer and relatively flexible so that it can enter into and perform massage in openings of unusual shape and situated in places that normally are virtually inaccessible.

While the wood can be utilized in its natural state and simply shaped as described, it is preferred that the wood be first dried and then bleached somewhat and smoothed. The wood can also be subjected to a dyeing operation in order that it can readily be observed by contrast against the teeth or against the gingiva. Some sort of flavor such as a natural citrus and mint flavor may be introduced into the wood, not for any particular stimulating effect but rather to induce pleasant use, especially by relatively young users.

It has been found that interdental stimulators of this sort are not unattractive to those who can benefit from their use, that they can be used a relatively long time despite absorbed moisture without splintering or fraying or breaking, and are contoured to afford easy access to the surfaces and openings in the human mouth.

I claim:

1. An interdental stimulator comprising a straight stick of clear wood elongated in the direction of the wood grain and for the most part being bounded by a top planar surface, a bottom planar surface, and two planar, lateral surfaces and being substantially rectangular in cross-section in a plane normal to said direction, one end portion of said stick being defined between said top planar surface and only two side surfaces, there being near the end of said stick a portion defined by said two mutually inclined, longitudinal, approximately planar but partly concave side surfaces, said side surfaces intersecting in a longitudinally extending bottom ridge inclined with respect to said direction and said side surfaces merging smoothly with said lateral surfaces, said end portion being substantially triangular in cross-section in a plane normal to said direction and being no greater in cross-sectional area than the cross-sectional area of said rectangular portion, said end portion also being truncated to form a planar surface inclined with respect to said direction, merging with said top planar surface and located opposite the bottom ridge apex of said triangular portion, and said end portion being of a size to be at least partly received in the normal interproximal spaces between human teeth.

2. A device as in claim 1 in which said bottom ridge at the apex of said triangular portion is inclined toward said top planar surface as said ridge approaches the rectangular portion of said stick.

3. A device as in claim 1 in which said stick is of European sycamore.